(12) United States Patent
 Ichikawa et al.

(10) Patent No.: US 9,101,511 B2
(45) Date of Patent: Aug. 11, 2015

(54) DISPOSABLE PANTS-TYPE WEARING ARTICLE

(75) Inventors: Makoto Ichikawa, Kagawa (JP); Kenichi Sasayama, Kagawa (JP); Hiroki Yamamoto, Kagawa (JP); Kazuo Ukegawa, Kagawa (JP); Akihide Ninomiya, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 151 days.

(21) Appl. No.: 13/823,442

(22) PCT Filed: Sep. 8, 2011

(86) PCT No.: PCT/JP2011/070513
§ 371 (c)(1),
(2), (4) Date: Mar. 14, 2013

(87) PCT Pub. No.: WO2012/043188
PCT Pub. Date: Apr. 5, 2012

(65) Prior Publication Data
US 2013/0172841 A1  Jul. 4, 2013

(30) Foreign Application Priority Data

Sep. 30, 2010  (JP) .................................. 2010-223228

(51) Int. Cl.
| | |
|---|---|
| *A61F 13/49* | (2006.01) |
| *A61F 13/15* | (2006.01) |
| *A61F 13/496* | (2006.01) |
| *A61F 13/539* | (2006.01) |

(52) U.S. Cl.
CPC ......... *A61F 13/15585* (2013.01); *A61F 13/496* (2013.01); *A61F 13/49061* (2013.01); *A61F 13/539* (2013.01)

(58) Field of Classification Search
CPC ... A61F 13/15; A61F 13/15707; A61F 13/47; A61F 13/4704; A61F 13/475; A61F 13/476; A61F 13/49; A61F 13/49004; A61F 13/49007; A61F 13/51478; A61F 13/56
USPC .......................... 604/386, 389, 391, 394, 402
See application file for complete search history.

(56) References Cited

U.S. PATENT DOCUMENTS

| | | | |
|---|---|---|---|
| 2005/0148988 A1 | 7/2005 | Kinoshita et al. | |
| 2010/0286646 A1 | 11/2010 | Takino et al. | |

FOREIGN PATENT DOCUMENTS

| | | |
|---|---|---|
| EP | 2186495 A1 | 5/2010 |
| JP | 432718 U | 3/1992 |
| JP | 07163617 A | 6/1995 |
| JP | 2003102785 A | 4/2003 |
| JP | 2006-051240 A | 2/2006 |
| JP | 2006525857 A | 11/2006 |
| JP | 4240463 B2 | 3/2009 |
| JP | 2009050651 A | 3/2009 |

OTHER PUBLICATIONS

PCT/JP2011/070513 International Search Report, dated Dec. 13, 2011, English translation.
Extended European Search Report mailed May 28, 2015, corresponding to European patent application No. 11828749.9.

*Primary Examiner* — Melanie Hand
(74) *Attorney, Agent, or Firm* — Lowe Hauptman & Ham, LLP

(57) ABSTRACT

Disclosed is a disposable pants-type wearing article improved to prevent panels joined to one another from being peeled off from each other. A disposable pants-type wearing article includes a front panel 7, a rear panel 8 and a intermediate panel 6 joined to respective outer surfaces of these two panels 7, 8. Opposite lateral portions 34 of the intermediate panel 6 are formed by joining a pair of sheets together with a second hot melt adhesive 62. Zones coated with the second hot melt adhesive 62 include high density coated zones 72 formed by relatively large application quantity per 1 m² and low density coated zones 71 formed by relatively small application quantity per 1 m². Opposite end regions 36, 37 of the intermediate panel 6 joined to the front panel 7 and the rear panel 8 are at least partially formed with the high density coated zones 72.

4 Claims, 8 Drawing Sheets

DISPOSABLE PANTS-TYPE WEARING ARTICLE

RELATED APPLICATIONS

The present application is a National Phase of PCT/JP2011/070513, filed Sep. 8, 2011, and is based on, and claims priority from, Japanese Application No. 2010-223228, filed Sep. 30, 2010.

TECHNICAL FIELD

The present invention relates to disposable pants-type wearing articles.

Disposable pants-type wearing articles including a front panel adapted to cover the wearer's ventral side, the rear panel adapted to cover the wearer's dorsal side and the intermediate panel adapted to cover the wearer's crotch region are known.

For example, JP 4240463 B (PTL 1) discloses a pants-type diaper including an annular belt member adapted to cover the wearer's front and rear waist regions and an absorbent structure adapted to cover the wearer's crotch region. The absorbent structure includes an outer sheet and a nonwoven fabric sheet joined to the outer surface of the outer sheet wherein transversely opposite lateral portions of the nonwoven fabric sheet are folded inwardly so as to form flaps. The outer surfaces of the respective flaps are joined to the surface of the belt member facing the outer surfaces of the respective flaps.

JP 2006-525857 A (PTL 2) discloses a disposable pull-on type garment including an annular elastic belt adapted to cover the wearer's front and rear waist regions and an absorbent structure adapted to cover the wearer's crotch region. The absorbent structure is formed along the side edges with the barrier leg cuffs extending in a longitudinal direction. Longitudinal opposite end regions of the absorbent structure are attached to the inner surface of the elastic belt.

JP 2006-51240 A (PTL 3) discloses a simplified diaper including an annular waist member adapted to be circumferentially kept in close contact with the wearer's waist and the crotch member adapted to cover the wearer's crotch region. The waist member is formed on its outer surface with fastening means by which longitudinally opposite end regions of the crotch member may be detachably fastened to the outer surface of the waist member.

CITATION LIST

Patent Literature

{PTL 1} JP 4240463 B
{PTL 2} JP 2006-525857 A
{PTL 3} JP 2006-51240 A

SUMMARY OF INVENTION

Technical Problem

In pants-type wearing articles, the wearer's toes are sometimes caught by an intermediate panel or the like defining the crotch region of the article when the wearer puts on the article. In such a situation, if the longitudinally opposite end regions of the intermediate panel are attached to the respective inner surfaces of the front panel covering the wearer's waist or if the opposite end regions are attached between the front panel and the outer sheet covering outer surface of the front panel and between the rear panel and the outer sheet covering outer surface of the rear panel, respectively, movements of the opposite end regions outward from the front panel and the rear panel may be inhibited and whereby peeling off of the opposite end regions of the intermediate panel from the front panel and/or the rear panel may be prevented. However, in the conventional wearing articles having the opposite end regions of the intermediate panel attached to the respective outer surfaces of the front panel and the rear panel, the opposite end regions of the intermediate panel might be peeled off from the front panel and/or the rear panel if the wearer's toes are caught by the intermediate panel when the wearer puts on the article.

An object of this invention is to provide a disposable pants-type wearing article improved so that the opposite end regions of the intermediate panel are not peeled off from the front panel and/or the rear panel when the wearer puts on the article, even where the disposable pants-type wearing article is configured to have the opposite end regions of the intermediate panel attached to the respective outer surfaces of the front panel and the rear panel.

Solution to Problem

According to this invention, there is provided a disposable pants-type wearing article having a longitudinal direction and a transverse direction being orthogonal to each other and including a front panel, a rear panel and an intermediate panel. The front panel and the rear panel are joined to each other along respective side edges opposed in the transverse direction to form a circumferentially continuous waist region. The intermediate panel is bent in a U-shape, and one of end regions of the intermediate panel is at least partially joined to the front panel on an outer surface of the waist region while a remainder of the end regions is at least partially joined to the rear panel on the outer surface of the waist region.

This invention further includes the following features:

the front panel, the rear panel and the intermediate panel respectively have inner surfaces facing the wearer's skin and outer surfaces facing away from the wearer's skin;

the intermediate panel includes lateral portions extending along both sides opposite in the transverse direction between the opposite end regions and a midsection defined between the opposite lateral portions wherein, at least between the opposite end regions, the lateral portions are folded onto the inner surface of the midsection with the inner surface lying inside and this inner surface is joined to itself with a first hot melt adhesive;

the lateral portions of the intermediate panel are formed by overlapping and joining at least two sheet members to each other with a second hot melt adhesive and a plurality of elastics attached under tension in the longitudinal direction between the two sheet members;

zones of the two sheet members coated with the second hot melt adhesive include high density coated zones in which an application quantity per 1 $m^2$ is relatively large and low density coated zones in which an application quantity per 1 $m^2$ is relatively small wherein the high density coated zones are formed at least in part of the opposite end regions.

According to one embodiment of this invention, the low density coated zones of the second hot melt adhesive are formed in ranges in the longitudinal direction of the lateral portions in which the elastics are interposed therein.

According to another embodiment of this invention, at the outer surfaces of the respective lateral portions folded and at the inner surface of the midsection extending between the lateral portions opposite in the transverse direction, the intermediate panel is joined to the front panel and the rear panel with a third hot melt adhesive.

According to still another embodiment of this invention, the front panel and the rear panel respectively have upper edges and lower edges in the longitudinal direction and a range in which the inner surfaces of the respective lateral portions and the inner surface of the midsection are joined together extend downward beyond the lower edge in at least one of the front panel and the rear panel.

Advantageous Effects of Invention

In the disposable pants-type wearing article according to this invention, the lateral portions of the intermediate panel joined to the respective outer surfaces of the front panel and the rear panel are formed by overlapping and joining at least two sheet members to each other with the second hot melt adhesive. The zones of these two sheet members coated with the second hot melt adhesive include the high density coated zones and the low density coated zones. The opposite end regions of the intermediate panel joined to the front panel and the rear panel are at least partially formed with the high density coated zones. In these end regions, the high density coated zones serve to prevent the possibility that the two sheet members might be peeled off from each other.

DESCRIPTION OF EMBODIMENTS

Taking a pants-type diaper as an example of disposable pants-type wearing articles, details of this invention will be described hereunder with reference to the accompanying drawings.

Figure 1:
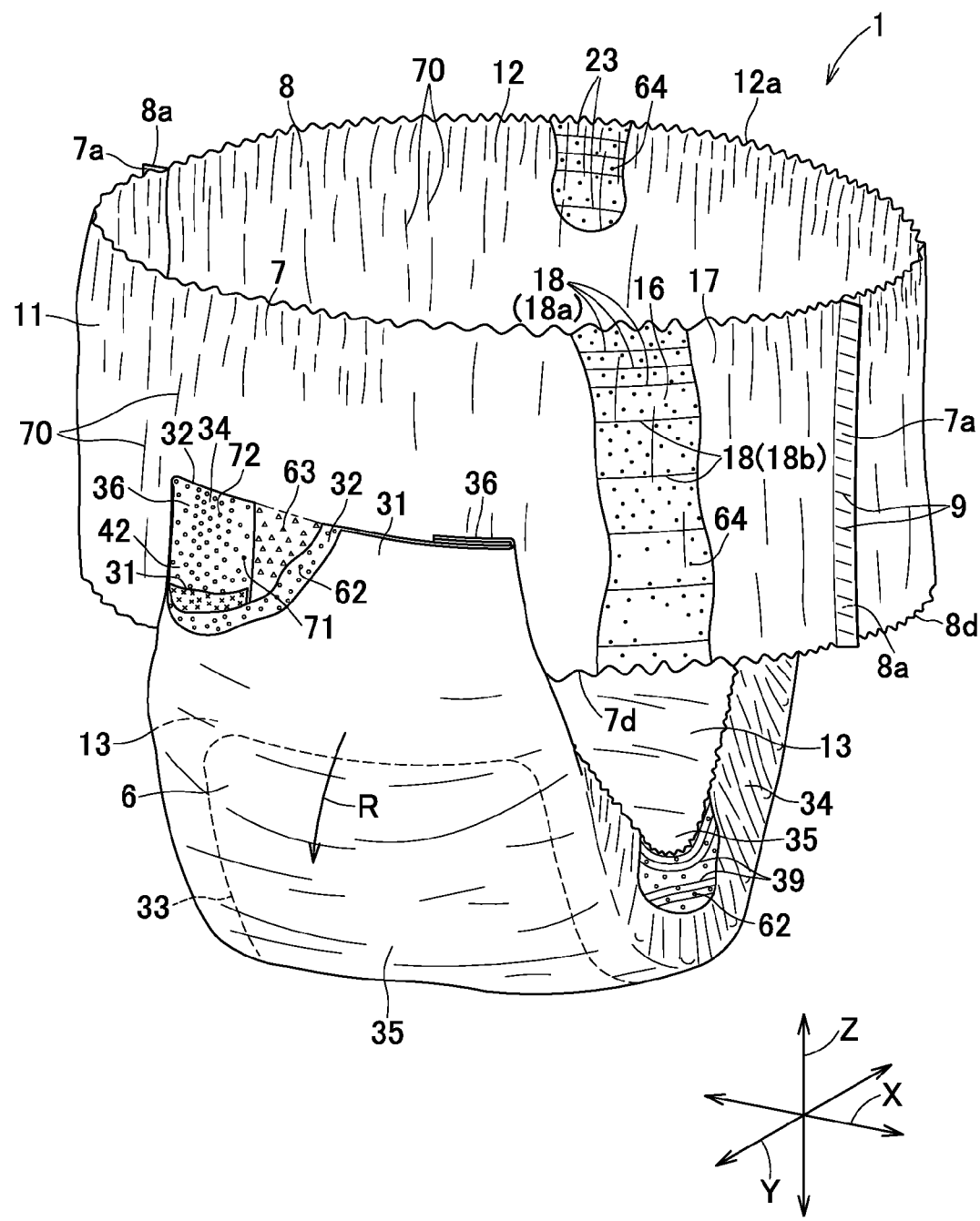
FIG. 1 is a partially cutaway perspective view of a disposable pants-type wearing article (diaper).

Referring to FIG. 1, it shows a partially cutaway perspective view of a disposable pants-type diaper 1 as an example of the disposable pants-type wearing article in the configuration it would assume when placed on a wearer. The diaper 1 includes a front panel 7, a rear panel 8 and an intermediate panel 6. The diaper 1 has a longitudinal direction Y and a transverse direction X wherein the front panel 7 extending forward in the longitudinal direction Y and the rear panel 8 extending rearward in the longitudinal direction Y are put flat together along respective side edges 7a, 8a thereof opposite in the transverse direction X and joined together at a pair of series of seams 9 to form an annular waist region 11 defining a waist-opening 12. The intermediate panel 6 is bent in a U-shape with front and rear end portions 42 (See FIG. 2) so as to oppose to each other back and forth. The front end 42 is joined to the front panel 7 on an outer surface of the waist region 11 with a third hot melt adhesive 63 while the rear end 43 is joined to the rear panel 8 on the outer surface of waist region 11 with the third hot melt adhesive 63 (See FIG. 2 also). The front and rear panels 7, 8 and the intermediate panel 6 are joined together to form a pair of leg-openings 13. The intermediate panel 6 includes leg elastics 39 adapted to extend nearly half around the respective leg-openings 13.

Referring further to FIG. 1, the front panel 7 includes an inner sheet 16 facing the wearer's skin (not shown), an outer sheet 17 facing the wearer's garment and front waist elastics 18 interposed between these inner and outer sheets 16, 17. The inner and outer sheets 16, 17 are attached to each other with a fourth hot melt adhesive 64 (See FIG. 2) and the front waist elastics 18 are joined to at least one of the inner and outer sheets 16, 17 under tension with hot melt adhesives (not shown). In FIG. 1, the front waist elastics 18 contract in a circumferential direction of the waist region 11 to form the outer sheet 17 with gathers 70 formed of small crests and troughs extending in the longitudinal direction.

Figure 2:
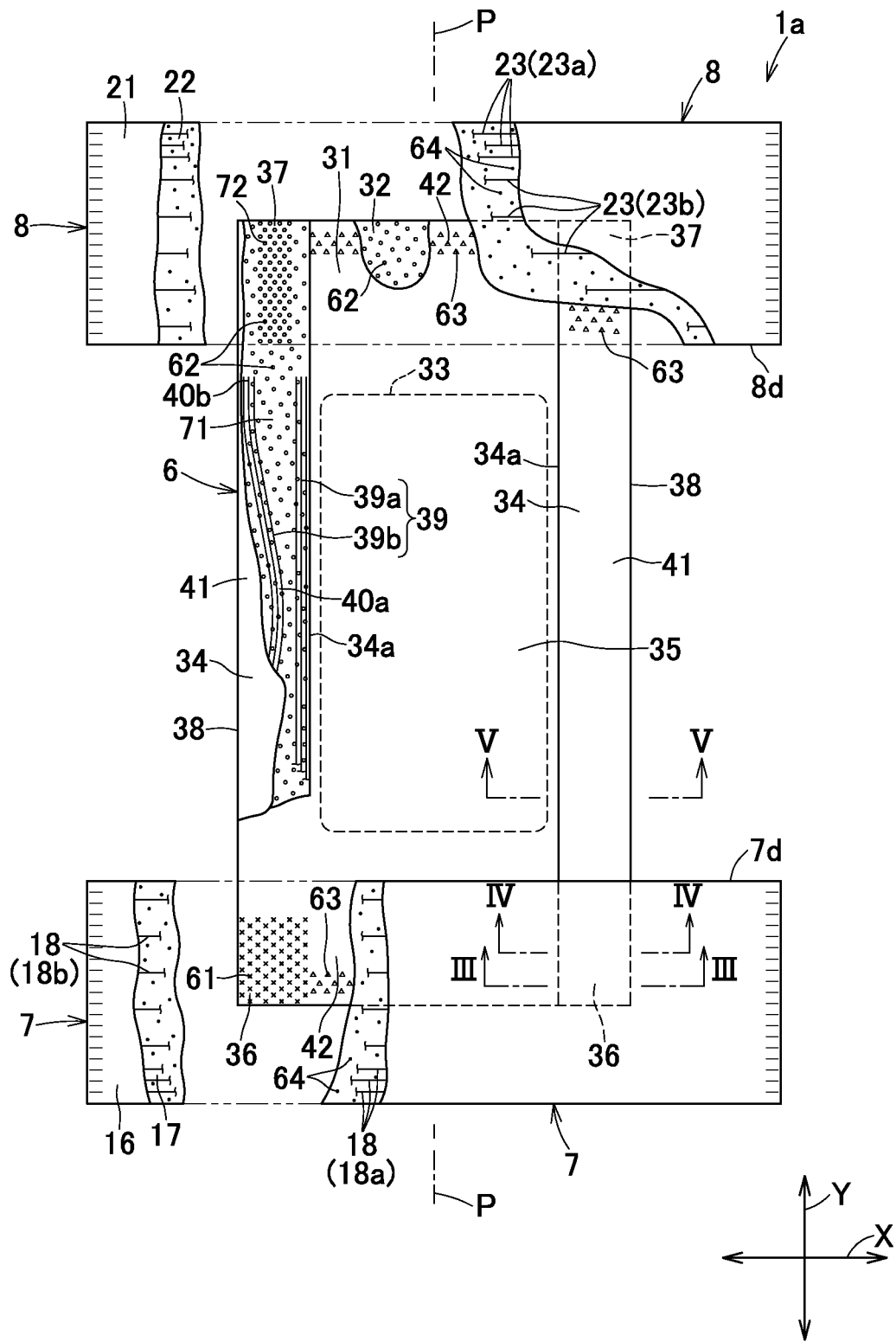
FIG. 2 is a partially cutaway plan view of a developed diaper.

Referring to FIG. 2, it shows a partially cutaway plan view of a developed diaper 1a assumed by peeling off the front panel 7 and the rear panel 7 from each other along the seams 9 and developing the front and rear panels 7, 8 and the intermediate panel 6 in the transverse direction X and the longitudinal direction Y. These front panel 7, rear panel 8 and intermediate panel 6 are formed symmetrically about a center line P-P bisecting a dimension of the developed diaper 1a about the center line P-P.

The front waist elastics 18 in the front panel 7 include a plurality of upper elastics 18a circumferentially extending along a peripheral edge 12a of the waist-opening 12 as viewed in FIG. 1, and narrowly spaced apart from each other in the longitudinal direction Y as viewed in FIGS. 1, 2, and similarly a plurality of lower elastics 18b circumferentially extending and, compared to the upper elastics 18d, widely spaced apart from each other in the longitudinal direction Y as viewed in FIG. 1. FIG. 2 shows the front waist elastics 18 stretched in the transverse direction X so as to maintain the air-permeable inner sheet 16 and the air-permeable outer sheet 17 in a flat state and, upon contraction of the front waist elastics 18, the air-permeable inner and outer sheets 16, 17 are formed with the gathers 70 as shown in FIG. 1.

The rear panel 8 shown in FIG. 2 includes an inner sheet 21 facing the wearer's skin, an air-permeable outer sheet 22 facing the wearer's garment and rear waist elastics 23 interposed between these inner and outer sheets 21, 22. The rear waist elastics 23 include a plurality of upper elastics 23a circumferentially extending along a peripheral edge 12a of the waist-opening 12 as viewed in FIG. 1 and narrowly spaced apart from each other in the longitudinal direction Y as viewed in FIGS. 1, 2, and a plurality of lower elastics 23b circumferentially extending and, compared to the upper elastics 23a, widely spaced apart from each other in the longitudinal direction Y as viewed in FIG. 1, 2. The inner and outer sheets 21, 22 are joined to each other with a fourth hot melt adhesive 64 and the rear waist elastics 23 are attached under tension in the transverse dimension X to at least one of the inner and outer sheets 21, 22 with hot melt adhesives (not shown). FIG. 2 shows the inner sheet 21 and the outer sheet 22 are maintained in a flat state and, upon contraction of the rear waist elastics 23, the inner and outer sheets 21, 22 are formed with the gathers 70 as shown in FIG. 1.

The intermediate panel 6 includes a liquid-pervious inner sheet 31, a liquid-impervious outer sheet 32 and a liquid-absorbent core 33 interposed between these two sheets 31, 32. The inner sheet 31 and the outer sheet 32 extend outwardly beyond a peripheral edge of the core 33 and are joined to each other outboard of the peripheral edge of the core 33 with a second hot melt adhesive 62 to form extensions 41 in the transverse direction and extensions 42 in the longitudinal direction. The extensions 41 in the transverse direction include lateral portions 34 of the intermediate panel 6 and these lateral portions 34 are folded inwardly along fold lines 38 extending in parallel to the center line P-P with respective inner surfaces of the respective lateral portions 34. In a midsection 35 of the intermediate panel 6, the inner sheet 31 defining the inner surface of the midsection 35 and the inner sheet 31 in the lateral portions 34 are joined to each other with a first hot melt adhesive 61 at front end regions 36 and the rear end regions 37 of the respective lateral portions 34. The front end regions 36 of the respective lateral portions 34 are the regions in which the front panel 7 and the midsection 35 overlap with each other by the intermediary of the lateral portions 34 and the rear end regions 37 are the regions in which the rear panel 8 and the midsection 35 overlap with each other by the intermediary of the lateral portions 34.

In the intermediate panel 6, a plurality of leg elastics 39 are interposed between at least two sheets forming the lateral portions 34, i.e., between the inner sheet 31 and the outer sheet 32. The leg elastics 39 include a plurality of first leg elastics 39a rectilinearly extending along edges 34a of the respective lateral portions 34 and a plurality of second leg elastics 39b extending in vicinities of the respective fold lines 38 so as to curve convexly toward the edges 34a. The first and second leg elastics 39a, 39b are attached under tension in the longitudinal direction Y to the inner sheet 31 and/the outer sheet 32 with hot melt adhesives (not shown) preferably without fully extending in the longitudinal direction Y to the front and rear end regions 36, 37. When the developed diaper 1a has been assembled to form the diaper 1 of FIG. 1 and put on the wearer's body, the midsection 35 of the intermediate panel 6 sags down and contraction of the leg elastics 39 causes intermediate regions of the respective lateral portions 34 defined between the front end regions 36 and the rear end regions 37 to be spaced apart from the midsection 35 toward the wearer's skin. When the second leg elastics 39b of the leg elastics 39 are attached to the inner sheet 31 or the outer sheet 32 of the lateral portions 34 so as to curve convexly toward the edges 34a, an extensibility of the second leg elastics 39b may be gradually changed between convex segments 40a formed along respective longitudinal midsections and rectilinear segments 40b formed along respective longitudinally opposite end regions. Specifically, the extensibility may be gradually reduced from the convex segments 40a toward the rectilinear segments 40b to keep the lateral portions 34 in close contact with the wearer's skin at a particularly high contact pressure in the vicinities of the convex segments 40a.

In these lateral portions 34, the second hot melt adhesive 62 used to join the inner sheet 31 and the outer sheet 32 to each other is quantitatively varied depending on zones to be coated so as to form low density coated zones 71 and high density coated zones 72. Specifically, an application quantity of the second hot melt adhesive 62 per 1 $m^2$ of the lateral portions 34 in the respective low density coated zones 71 is adjusted to be smaller than an application quantity in the high density coated zones 72. Referring to FIG. 2, the low density coated zones 71 are formed preferably between the front panel 7 and the rear panel 8 in the longitudinal direction Y of the lateral portions 34 to prevent problems such that the presence of the second hot melt adhesive 62 might deteriorate a flexibility of the zones likely to come in contact with the wearer's skin and that stretching and contracting properties of the leg elastics 39 in such zones might be deteriorated. The high density coated zones 72 are formed at least in part of the front end regions 36 and the rear end regions 37 in the respective lateral portions 34 in order to prevent the inner sheet 31 and the outer sheet 32 from being peeled off each other when the diaper 1 is put on the wearer's body. While it is possible to form the high density coated zones 72 so as to occupy the respective entire areas of the front end regions 36 and the rear end regions 37, these high density coated zones 72 are formed only in middle zones of the respective regions 36, 37 as viewed in the transverse direction X in the illustrated embodiment. While the low density coated zones 71 are formed at locations on respective extensions of the leg elastics 39a, 39b in the illustrated embodiment, it is possible to form the high density coated zones 72 at locations on respective extensions of the leg elastics 39a, 39b so long as the leg elastics 39a, 39b extend across or into these locations. With such an arrangement, these leg elastics 39a, 39b can be securely retained in the intermediate segments of the respective lateral portions 34 defined between the front end regions 36 and the rear end regions 37. The high density coated zones 72 securely join the lateral portions 34 to the midsection 35 of the intermediate panel 6 but may make the zones occupied by the high density zones 72 less flexible. However, in the diaper 1 according to this invention, even if such zones made less flexible due to the presence of the high density coated zones 72, the high density coated zones 72 are defined on the outer side of the front panel 7 and the rear panel 8 and not in contact with the wearer's skin.

Figure 3:
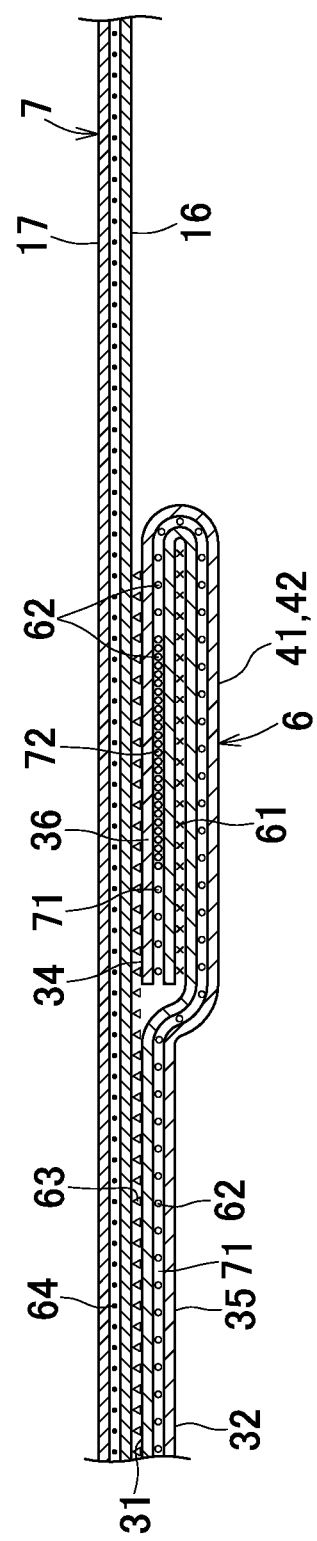
FIG. 3 is a sectional view taken along line III-III in FIG. 2.

Referring to FIG. 3, it shows a sectional view taken along line in FIG. 2. In the front end region 36 of the lateral portion 34, the zone coated with the first hot melt adhesive 61 is formed between the lateral portion 34 and the midsection 35 and the lateral portion 34 is formed with the high density coated zone 72 with the second hot melt adhesive 62 in the same manner as in the rear end region 37 wherein the low density coated zones 72 are formed on both sides of the high density coated zone 71. For reference's sake, FIG. 3 shows the portion of the intermediate panel 6 including the transverse extension 41 and the longitudinal extension 42.

Referring further to FIG. 3, the inner surface of the lateral portion 34 and the inner surface of the intermediate panel 6 in its midsection 35 are joined to each other with the first hot melt adhesive 61. In the midsection 35, the inner sheet 31 and the outer sheet 32 are joined to each other with the second hot melt adhesive 62 defining here the low density coated zone 71. The intermediate panel 6 is joined to the front panel 7 with the third hot melt adhesive 63. In the front panel 7, the air-permeable inner sheet 16 and the air-permeable outer sheet 17 are joined to each other with the fourth hot melt adhesive 64.

Figure 4:
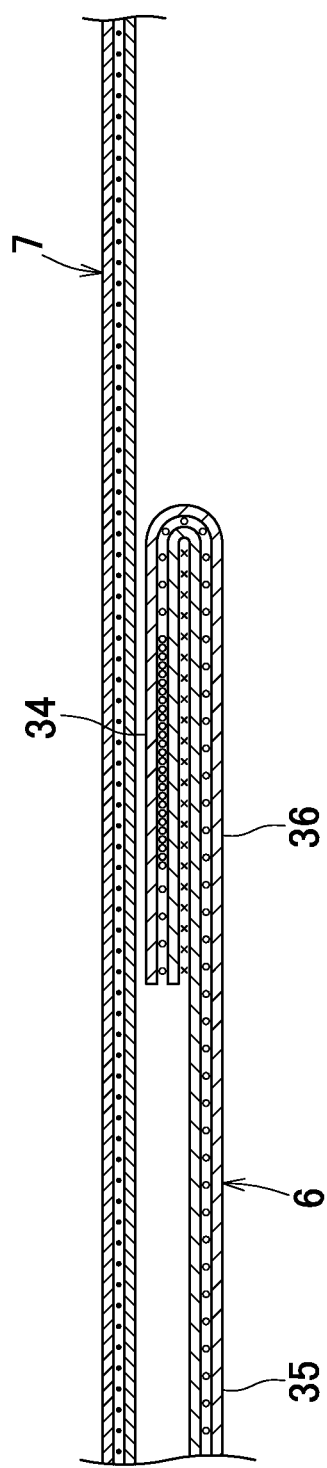
FIG. 4 is a sectional view taken along line IV-IV in FIG. 2.

Referring to FIG. 4, it shows a sectional view taken along line IV-IV in FIG. 2 and line IV-IV extend regions in a vicinity of a lower edge 7d (See FIG. 1) of the front panel 7. In the front end region 36 of the lateral portion 34 shown in FIG. 4, the intermediate panel 6 and the front panel 7 are not joined to each other and FIG. 1 also shows the diaper 1 in such a state that the intermediate panel 6 can be readily separated from the front panel 7. The other arrangements of the intermediate panel 6 and the front panel 7 are similar to those shown in FIG. 3.

Figure 5:
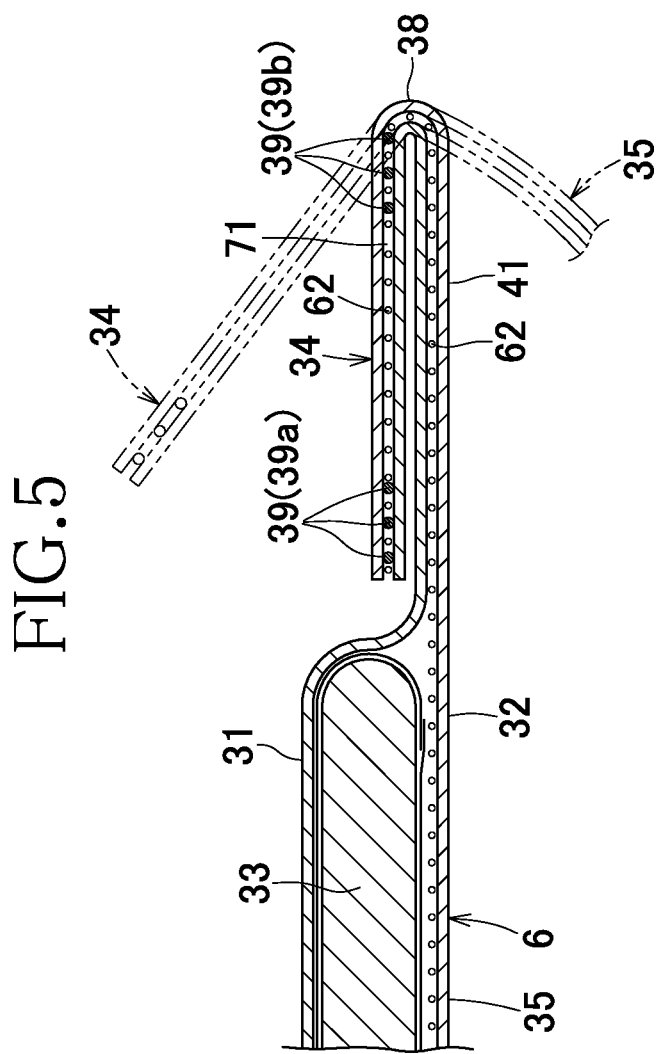
FIG. 5 is a sectional view taken along line V-V in FIG. 2.

Referring to FIG. 5, it shows a sectional view taken along line V-V in FIG. 3. The intermediate panel 6 shown herein includes the bodily fluid absorbent core 33 and one of the transverse extensions 41. The transverse extension 41 is partially folded along the fold line 38 to form the lateral portion 34 inclusive of the leg elastics 39. In the lateral portion 34, the second hot melt adhesive 62 forms the low density coated zone 71. The midsection 35 of the intermediate panel 6 includes the bodily fluid absorbent core 33 and part of the transverse extension 41. When the developed diaper 1a is assembled to form the diaper 1 of FIG. 1, the midsection 35 sags down as indicated by imaginary lines and the lateral portion 34 spaced upwardly as indicated by imaginary lines under contraction of the leg elastics 39.

In the diaper 1 and the developed diaper 1a formed in the above-mentioned manner, as the first to fourth hot melt adhesives 61-64, various types of hot melt adhesives commonly used in the relevant technical field such as hot melt adhesives of styrene type, styrene/butadiene type, styrene/butadiene/styrene type and acrylic type may be selectively used. As means for coating of the first to fourth hot melt adhesives 61-64, various types of coater commonly used in the relevant technical field such as a spiral spray coater and a bar coater may be selectively used and various coating patterns such as a dotted pattern, a spiral pattern and a beaded pattern may be selectively adopted. An application quantity of the hot melt adhesives is preferably in a range of 5 to 30 g per 1 $m^2$ of the area to be joined. Concerning the second hot melt adhesive 62, an application quantity thereof is preferably adjusted so that the application quantity thereof is in a range of 0.3 to 3 g per 1 $m^2$ in the low density coated zone 71 and in a range of 5 to 30 g per 1 $m^2$ in the high density coated zone 72.

When the diaper 1 of FIG. 1 is put on the wearer's body, sometimes the wearer's toes may be caught by the lateral portions 34 or may push the midsection 35 of the intermediate panel 6 outwardly of the diaper 1. If such trouble occurs with the front panel 7 and the rear panel 8 still gripped by both hands of the wearer or a care personnel, the intermediate panel 6 may be subjected to an action, for example, to move the intermediate panel 6 in a direction indicated by an arrow R in FIG. 1 from the front panel 7, thereby peeling the intermediate panel 6 off from the front panel 7, or to peel the midsection 35 off the lateral portions 34, or to peel the inner sheet 31 and the outer sheet 32 off from each other along the lateral portions 34. To prevent the respective sheets from being peeled off each other under such action, a countermeasure may be taken so as to increase the application quantity of the first to fourth hot melt adhesives 61-64 and to enlarge the area coated therewith in the diaper 1. However, if such countermeasure is simply applied to the inner sheet 31 and the outer sheet 32 of the lateral portions 34, the lateral portions 34 might be deteriorated in flexibility. In the wearing article according to this invention exemplified in FIG. 1 in the form of the diaper 1, the second hot melt adhesive 62 is quantitatively varied depending on the zones to be coated so as to form low density coated zones 71 and high density coated zones 72 and thereby the above-mentioned problem may be prevented.

Figure 6:
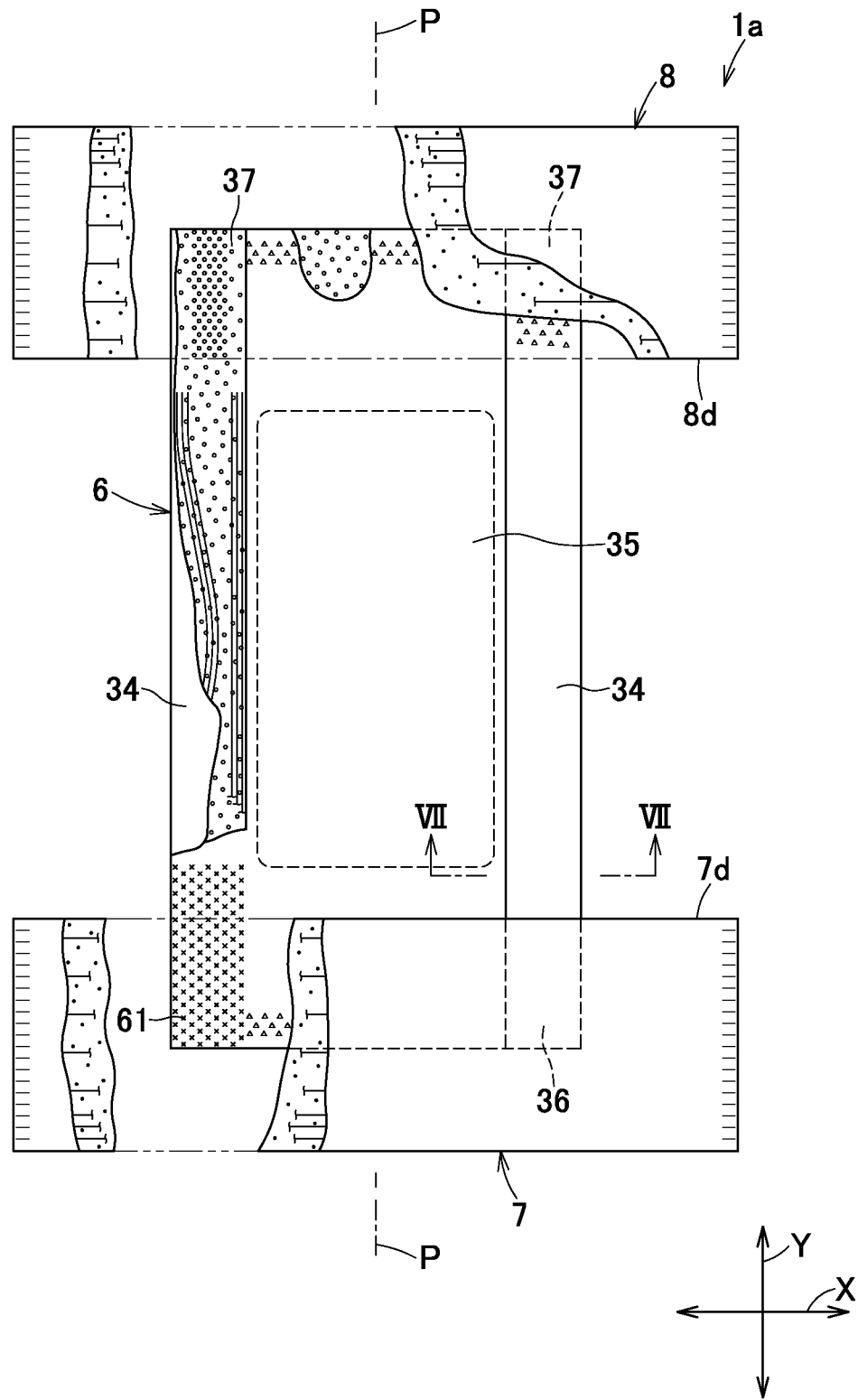
FIG. 6 is a view similar to FIG. 2, showing one embodiment.
Figure 7:
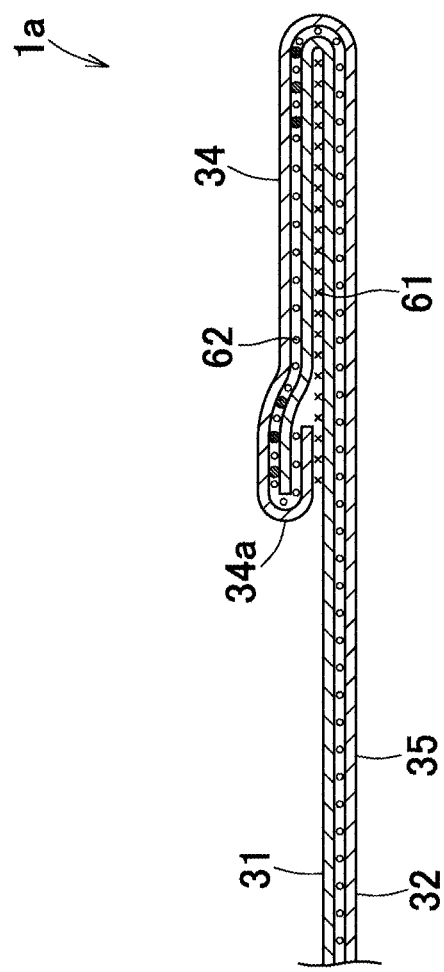
FIG. 7 is a sectional view taken along line VII-VII in FIG. 6.

Referring to FIG. 6, it shows a view similar to FIG. 2, as one embodiment of this invention and referring to FIG. 7, it shows a sectional view taken along line VII-VII in FIG. 6 wherein FIG. 7 is the view similar to FIG. 5. It should be noted here that the developed diaper 1a of FIG. 6 is distinguished from the developed diaper 1a of FIG. 2 in that the zones coated with the first hot melt adhesive 61 formed to join the lateral portions 34 to the midsection 35 in the intermediate panel 6 extend regions not only across the front end regions 36 of the respective lateral portions 34 but also toward the rear panel 8 beyond the lower edge 7d of the front panel 7. Though not shown, this is true for the zones coated with the first hot melt adhesive 61 in the rear end regions 37 of the respective lateral portions 34, i.e., the zones coated with the first hot melt adhesive 61 extend regions not only across the rear end regions 37 but also toward the front panel 7 beyond the lower edge 8d (See FIGS. 1 and 2). With the diaper 1 arranged in this manner, it is possible to improve a preventive effect against peeling off of the lateral portions 34 and the midsection 35 which might otherwise occur when the wearer puts the diaper 1 on the wearer's body or during use of the diaper 1. Arrangement of the outer sheet 32 along the lateral portions 34 in FIG. 7 is distinguished from the arrangement of the outer sheet 32 in FIG. 5 in that the outer sheet 32 is folded along the edges 34a of the respective lateral portions 34 onto the inner sheet 31 and joined thereto with the second hot melt adhesive 62.

Figure 8:
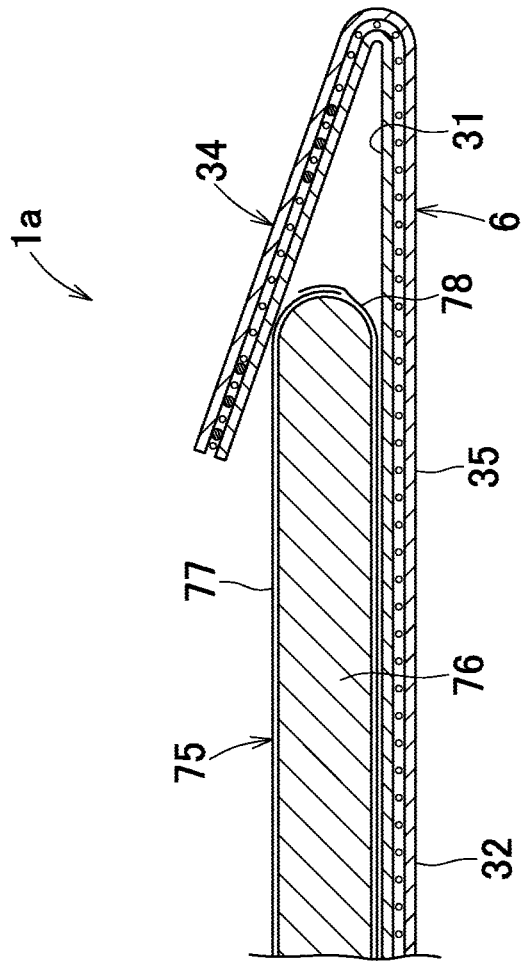
FIG. 8 is a view similar to FIG. 5, showing another embodiment.

Referring to FIG. 8, it shows a view similar to FIG. 5, as another embodiment of this invention. In the developed diaper 1a arranged as shown in FIG. 8, the core 33 exemplified in FIGS. 2 and 5 is not included between the inner sheet 31 and the outer sheet 32 of the intermediate panel 6 but a bodily fluid absorbent pad 75 which is an alternative to the core 33 and has a transverse dimension larger than that of the core 33 is disposed on the inner surface of the intermediate panel 6 by partially inserting the pad 75 between the lateral portions 34 and the midsection 35. The pad 75 is formed by sandwiching a bodily fluid absorbent core 76 between a liquid-pervious inner sheet 77 and a liquid-impervious outer sheet 78. The pad 75 is adapted to be detachably disposed on the intermediate panel 6 and, if desired, the pad 75 may be coated on its region facing the intermediate panel 6 with pressure-sensitive adhesive or a mechanical fastener may be attached to this region to stabilize the pad 75 disposed on the intermediate panel 6. The diaper 1 obtained from such developed diaper 1a may be termed as the diaper having the exchangeable pad 75 or the diaper cover for use of the pad 75.

In the diaper 1 and the developed diaper 1a exemplified, appropriate materials of the topsheet 16 and the outer sheet 17 of the front panel 7 as well as the inner sheet 21 and the outer sheet 22 of the rear panel 8 may be selected from a group including nonwoven fabrics formed of thermoplastic synthetic fibers, plastic films and laminated sheets formed of these nonwoven fabrics and plastic films. Appropriate materials of the inner sheet 31 in the intermediate panel 6 may be selected from a group including liquid-pervious nonwoven fabrics formed of thermoplastic synthetic fibers and perforated plastic films. While the outer sheet 32 may be formed of a liquid-impervious plastic film alone, a nonwoven fabric formed of thermoplastic synthetic fibers may be laminated on the outer surface of the plastic film to provide the outer surface of the intermediate panel 6 with a cloth-like texture. The nonwoven fabric laminated plastic film may be dimensioned to be slightly larger than the core 33 in the transverse direction X as well as in the longitudinal direction Y as viewed in FIG. 2 to use the nonwoven fabric laminated on the plastic film as the inner sheet 31 in the respective transverse extension 41. Both the core 33 in FIG. 2 and the core 76 of the pad 75 in FIG. 8 may be obtained by wrapping an assembly of liquid-absorbent materials such as fluff wood pulp or a mixture of fluff wood pulp and superabsorbent polymer particles with tissue paper or a wrapping sheet formed of a liquid-pervious nonwoven fabric.

REFERENCE SIGNS LIST 1 disposable pants-type wearing article (diaper))
6 intermediate panel
7 front panel
8 rear panel
34 lateral portions
35 midsection
36 end region
37 end region
61 first hot melt adhesive
62 second hot melt adhesive
71 low density coated zone
72 high density coated zone
X transverse direction
Y longitudinal direction
Z longitudinal direction

The invention claimed is:

1. A disposable pants-type wearing article having a longitudinal direction and a transverse direction being orthogonal to each other, said wearing article comprising:
   a front panel;
   a rear panel; and
   an intermediate panel,
   wherein
   the front panel and the rear panel are joined to each other along respective side edges opposed in the transverse direction to form a circumferentially continuous waist region,
   the intermediate panel is bent in a U-shape,
   one of opposite end regions of the intermediate panel is at least partially joined to the front panel on an outer surface of the waist region, while another one of the opposite end regions is at least partially joined to the rear panel on the outer surface of the waist region,
   the front panel, the rear panel and the intermediate panel respectively have
      inner surfaces configured to face a wearer's skin, and
      outer surfaces configured to face away from the wearer's skin,
   the intermediate panel includes
      lateral portions opposite each other in the transverse direction and extending between the opposite end regions; and
      a midsection defined between the opposite lateral portions,
   at least between the opposite end regions, the lateral portions are folded onto the inner surface of the midsection with the inner surface lying inside and joined to itself with a first hot melt adhesive,
   the lateral portions of the intermediate panel include
      at least two sheet members overlapping and joined to each other with a second hot melt adhesive; and
      a plurality of elastics attached under tension in the longitudinal direction between the two sheet members
   zones of the two sheet members coated with the second hot melt adhesive comprise
      high density coated zones in which an application quantity of the second hot melt adhesive per 1 $m^2$ is relatively large; and
      low density coated zones in which an application quantity of the second hot melt adhesive per 1 $m^2$ is relatively small, and
   the high density coated zones are arranged at least in part of the opposite end regions and between adjacent low density coated zones in the transverse direction.

2. The wearing article defined by claim 1, wherein the low density coated zones of the second hot melt adhesive extend in the longitudinal direction in the lateral portions in which the elastics are interposed.

3. The wearing article defined by claim 1, wherein at the outer surfaces of the respective lateral portions folded and at the inner surface of the midsection, the intermediate panel is joined to the front panel and the rear panel with a third hot melt adhesive.

4. The wearing article defined by claim 1, wherein
   the front panel and the rear panel respectively have upper edges and lower edges in the longitudinal direction, and
   an area in which the inner surfaces of the respective lateral portions and the inner surface of the midsection are joined together extends downward beyond the lower edge of at least one of the front panel and the rear panel.

* * * * *